US010941239B2

(12) United States Patent
Mes et al.

(10) Patent No.: US 10,941,239 B2
(45) Date of Patent: Mar. 9, 2021

(54) SUPRAMOLECULAR BIODEGRADABLE POLYMER

(71) Applicant: SupraPolix B.V., Eindhoven (NL)

(72) Inventors: Tristan Mes, Eindhoven (NL); Anton Willem Bosman, Eindhoven (NL)

(73) Assignee: SUPRAPOLIX B.V., Eindhoven (NL)

( * ) Notice: Subject to any disclaimer, the term of this patent is extended or adjusted under 35 U.S.C. 154(b) by 0 days.

(21) Appl. No.: 16/435,272

(22) Filed: Jun. 7, 2019

(65) Prior Publication Data

US 2019/0359760 A1 Nov. 28, 2019

Related U.S. Application Data

(63) Continuation of application No. 14/891,111, filed as application No. PCT/NL2014/050304 on May 14, 2014, now Pat. No. 10,358,522.

(30) Foreign Application Priority Data

May 14, 2013 (EP) .................................. 13167638

(51) Int. Cl.
| | | |
|---|---|---|
| *C08G 18/66* | (2006.01) | |
| *C08L 101/00* | (2006.01) | |
| *C08G 83/00* | (2006.01) | |
| *C08G 18/10* | (2006.01) | |
| *C08G 18/12* | (2006.01) | |
| *A61L 27/18* | (2006.01) | |
| *A61L 27/58* | (2006.01) | |
| *C08G 18/73* | (2006.01) | |

(52) U.S. Cl.
CPC .......... *C08G 18/6607* (2013.01); *A61L 27/18* (2013.01); *A61L 27/58* (2013.01); *C08G 18/10* (2013.01); *C08G 18/12* (2013.01); *C08G 18/664* (2013.01); *C08G 18/6637* (2013.01); *C08G 18/6674* (2013.01); *C08G 18/73* (2013.01); *C08G 83/008* (2013.01); *C08L 101/005* (2013.01); *C08G 2230/00* (2013.01)

(58) Field of Classification Search
CPC .............. C08G 18/6607; C08G 18/664; C08G 18/6674; C08G 18/12; C08G 18/73; C08G 18/10; C08G 83/008; C08G 18/6637; C08G 2230/00; A61L 27/18; A61L 27/58; C08L 101/005

See application file for complete search history.

(56) References Cited

U.S. PATENT DOCUMENTS

| | | | |
|---|---|---|---|
| 6,320,018 B1 | 11/2001 | Sijbesma et al. | |
| 10,358,522 B2 * | 7/2019 | Mes ...................... | C08G 18/10 |
| 2004/0087755 A1 | 5/2004 | Eling et al. | |
| 2007/0093639 A1 * | 4/2007 | Jassen .................. | C08G 18/714 |
| | | | 528/327 |
| 2008/0260795 A1 * | 10/2008 | Baughman ............... | A61K 9/06 |
| | | | 424/423 |
| 2009/0130172 A1 | 5/2009 | Dankers et al. | |
| 2012/0116014 A1 | 5/2012 | Janssen et al. | |

FOREIGN PATENT DOCUMENTS

| | | | |
|---|---|---|---|
| EP | 2450394 | * | 5/2012 |
| EP | 2 450 394 A1 | | 9/2012 |

OTHER PUBLICATIONS

Dankers et al., "A modular and supramolecular approach to bioactive scaffolds for tissue engineering", Nature, Jul. 2005, vol. 4, pp. 568-574.
Dankers et al., "Chemical and biological properties of supramolecular polymer systems based on oligocaprolactones" Biomaterials, 2006, vol. 27, pp. 5490-5501.
Dankers et al., "Novel biocompatible supramolecular materials for tissue engineering", Polymeric Materials: Science & Engineering, 2003, vol. 88, No. 52, pp. 1-2.
Sijbesma et al., "Reversible polymers formed from self-complementary monomers using quadruple hydrogen bonding", Science, vol. 278, Nov. 28, 1997, pp. 1601-1604.
Sontjens et al., "Thermoplastic elastomers based on strong and well-defined hydrogen-bonding interactions", Macromolecules, Jul. 11 2008, pp. 1-14.
Uhrich et al., "Polymeric systems for controlled drug release", Chemical Reviews, 1999, vol. 99, No. 11, pp. 3181-3198.
International Search Report issued in International Patent Application No. PCT/NL2014/050304 dated Jul. 7, 2014.

* cited by examiner

*Primary Examiner* — Rabon A Sergent
(74) *Attorney, Agent, or Firm* — Foley & Lardner LLP

(57) ABSTRACT

The present invention relates to a supramolecular biodegradable polymer comprising a quadruple hydrogen bonding unit (abbreviated herein as "4H-unit"), a biodegradable backbone and hard blocks and a process for preparing such a supramolecular biodegradable polymer. The supramolecular polymer is specifically suitable for biodegradable articles such as biomedical implants that need high strength and/or elasticity, e.g. medical implants in the cardio-vascular field.

16 Claims, No Drawings

SUPRAMOLECULAR BIODEGRADABLE POLYMER

FIELD OF THE INVENTION

The present invention relates to a supramolecular biodegradable polymer comprising a quadruple hydrogen bonding unit (abbreviated herein as "4H-unit"), a biodegradable backbone and hard blocks, which display superior mechanical strength and elasticity while keeping its ease of processing. The resulting supramolecular polymers according to the invention are specifically suitable for biodegradable articles such as biomedical implants that need high strength and/or elasticity, e.g. medical implants in the cardio-vascular field.

BACKGROUND OF THE INVENTION

A wide variety of biodegradable (also often designated as bioresorbable or biomedical) materials are known that are mostly based on aliphatic polyesters (Uhrich et al., Chem. Rev. 99, 3181-3198, 1999). The mechanical properties of current biodegradable materials are strongly related to their high molecular weights that are in general over 100 kDa, the presence of chemical cross-links, and the presence of crystalline domains in these polymers. Although the crystalline domains are beneficial for the initial high strength of the material, they do have a strong impact on the biodegradation process of the material as the biodegradation of crystalline domains is in general very slow and crystalline domains may cause immunological responses. Moreover, the need for high molecular weight polymers, in order to get the desired material properties, usually implies that high processing temperatures are required, and these are unfavourable as thermal degradation processes become more likely. Additionally, the crystalline domains may have a negative impact on the long term elastic behaviour of the material due to their tendency to induce fatigue characteristics.

The present invention relates to a supramolecular biodegradable polymer that comprises 4H-units that are capable of forming at least four H-bridges in a row, preferably with another 4H-unit, leading to physical interactions between different polymer chains. The physical interactions originate from multiple hydrogen bonding interactions (supramolecular interactions) between individual 4H-units or between a 4H-unit and another moiety capable of forming hydrogen bonds thereby forming self-complementary units, preferably comprising at least four hydrogen bonds in a row.

Units capable of forming at least four hydrogen bonds in a row, i.e. quadruple hydrogen bonding units, are in this patent application abbreviated as "4H-units". Sijbesma et al. (U.S. Pat. No. 6,320,018; Science 278, 1601-1604, 1997; both incorporated by reference) discloses 4H-units that are based on 2-ureido-4-pyrimidones. These 2-ureido-4-pyrimidones in their turn are derived from isocytosines.

A low molecular weight telechelic polycaprolactone (PCL) end-capped with 4H-units is disclosed in Dankers et al. (Polymeric Materials Sci. & Eng. 88, 52, 2003; Nature Materials 4, 5688, 2005 both incorporated by reference). It was found that films of this material were biocompatible based on the observed attachment of fibroblast cells to the films. The study on the biodegradation of this polymer showed the presence of crystallites, which is not favourable for bioresorption. Moreover, DSC-thermograms revealed the highly crystalline nature of the PCL backbone. The same PCL material and PCL materials comprising several 4H-units along the backbone are further characterized on their mechanical behaviour in Dankers et al. (Biomaterials 27, 5490, 2006; incorporated by reference). This study revealed that the highly crystalline telechelic PCL with 4H-units has a Young's modulus of about 130 MPa but breaks already after about 14% elongation. Whereas, the much less crystalline chain extended PCL-derivative with 4H-units has a lower Young's modulus of only about 3 MPa and an elongation of break of 576% (cf. Table 1 on page 5495). Both materials have only one melting point above 40° C. for the pristine non-annealed materials.

US 2009/00130172, incorporated by reference, discloses several biodegradable materials that comprise 4H-units mixed with bioactive molecules comprising a 4H-unit for biomedical applications such as coatings with controlled release of drugs. Among the materials disclosed are the materials as published by Dankers et al. mentioned above, as well as other biodegradable polyester derivatives comprising 4H-units, notable the telechelic PCL of Dankers et al. in Example 14, and the chain extended PCL and polyadipate-based polymers with isophorone diisocyanate (IPDI) in Examples 8, 12, 13, and 15. However, all these polyester based materials are characterized by poor mechanical behaviour, either not strong enough (modulus lower than 10 MPa) or not elastic enough (elongation below 50%).

Söntjens et al. (Macromolecules 41, 5703, 2008; incorporated by reference) disclose the above mentioned polyadipate-based polymers which are chain extended with 4H-units, as well as their analogues with 1,6-hexamethylene diisocyanate (HDI). These materials are said to be suitable for biomedical applications e.g. in medical devices and tissue engineering. However, the IPDI-analogue has no thermal transition in DSC above 40° C. whereas the HDI-analogue has only one melting point above 40° C. Additionally, the materials have only a limited strength, with Young's moduli of about 1 and about 8 MPa for the IPDI-analogue and HDI-analogue, respectively, and tensile strengths below 3 MPa.

US 2004/0087755, incorporated by reference, discloses polyurethane based polymers end-capped with 4H-units, alkyl diol chain extenders, and 4,4'-methylene bis(phenyl isocyanate) (MDI), which can be used as hot melt adhesive or TPU foam. These materials have limited tensile strengths ranging from 2 to 8 MPa (Table 2) or stresses at 100% elongation between 2 to 4 MPa (Table 6). Most importantly, the aromatic MDI in these polyurethane materials hamper their possible use as biodegradable biomedical materials, since MDI is known to result in degradation products that can comprise highly toxic aniline and derivatives thereof.

US 2012/116014, incorporated by reference, discloses a process for the preparation of a supramolecular polymer comprising 1-50 4H-units, in which a 4H building block according to the formula 4H-(L-F$_i$)$_r$, wherein 4H represents a 4H-unit, L represents a divalent, trivalent, tetravalent or pentavalent linking group, F$_i$ represents a reactive group, and r is 1-4, is reacted with a prepolymer comprising a complementary reactive group, wherein the reaction mixture comprising said 4H building block and said prepolymer comprises less than 10 wt. % of a non-reactive organic solvent, based on the total weight of the reaction mixture. Most preferably, r is 2 and L is a divalent $C_1$-$C_{20}$ alkylene, arylene, arylalkylene or alkylarylene group, which implies that the 4H building block is preferably represented by the formula 4H-(L-F$_i$)$_2$. The 4H building block is preferably prepared from a precursor of an isocytosine or a melamine derivative and a diisocyanate, wherein the diisocyanate is most preferably isophorone diisocyanate (IPDI) or methylene dicyclohexane 4,4'-diisocyanate (HMDI). The supramolecular polymer according to US 2012/116014 is preferably used in coating and adhesive compositions. However, supramolecular polymers obtained according to this preferred process are too stiff (high Young's modulus) and have a low elasticity.

Hence there is a need in the art for supramolecular biodegradable materials for biomedical applications that have a high strength and/or a high elasticity. Furthermore, it is desired that they can easily be prepared and processed in a biomedically acceptable way.

It is therefore an object of the present invention to provide strong supramolecular biodegradable polymers as well as a process to prepare such polymers. The supramolecular biodegradable polymers according to the present invention have better material characteristics than those of the prior art without compromising the beneficial processing properties of supramolecular polymers. It is another object of the present invention to provide strong supramolecular biodegradable polymers used in biomedical implants and scaffolds for tissue engineering.

SUMMARY OF THE INVENTION

The present invention relates to a supramolecular biodegradable polymer comprising structural units A, B, C and F or comprising structural units A, B, C and G, wherein:
structural units A are represented by divalent organic groups —P—, wherein P is a polymeric group having a $M_n$ of about 250 to about 50,000;
structural units B are represented by divalent organic groups —$R^5$—, wherein $R^5$ is selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups may be interrupted by 1-5 heteroatoms selected from the group consisting of O, N and S;
structural units C are represented by divalent organic groups —$R^6$—, wherein $R^6$ is selected from the group consisting of $C_2$-$C_{20}$ alkylene;
structural units F are independently selected from the group consisting of units according to Formulas (1), (2), (3) and (4):

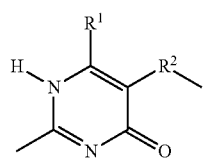
(1)

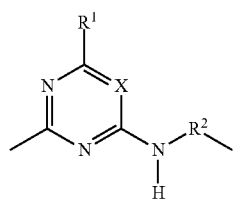
(2)

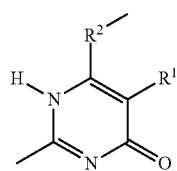
(3)

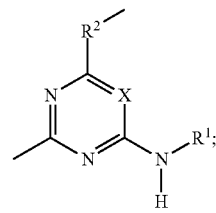
(4)

structural units G are independently selected from the group consisting of terminal units according to Formulas (5) and (6):

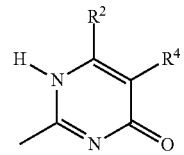
(5)

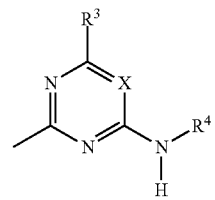
(6)

X is N or $CR^1$;
$R^1$, $R^3$ and $R^4$ are independently selected from the group consisting of:
(a) hydrogen;
(b) $C_1$-$C_{20}$ alkyl;
$R^2$ is selected from the group consisting of $C_1$-$C_{20}$ alkylene; and
wherein structural units A, B, C, F and G are bonded to each other via groups independently selected from urethane and urea groups and wherein F and G are bonded via the 2-position by a urea moiety.

The present invention also relates to a supramolecular biodegradable polymer that is obtainable by a process wherein:
a compound F' independently selected from the group consisting of Formulas (7), (8), (9) and (10), or a mixture thereof:

(7)

(8)

-continued

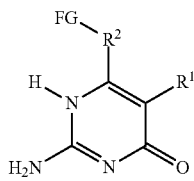

(9)

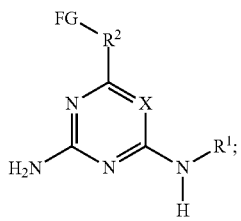

(10)

or
a compound G' independently selected from the group consisting of Formulas (11) and (12), or a mixture thereof:

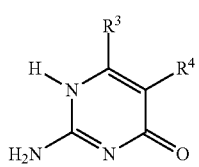

(11)

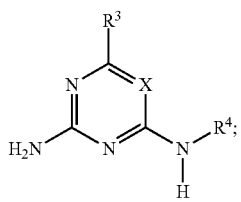

(12)

is reacted with:
a diisocyanate compound C' according to the Formula OCN—$R^6$—NCO;
a polymer A' according to the Formula FG-P-FG; and
a compound B' according to the Formula FG-$R^5$-FG;
wherein:
X is N or $CR^1$;
$R^1$, $R^3$ and $R^4$ are independently selected from the group consisting of:
(a) hydrogen;
(b) $C_1$-$C_{20}$ alkyl;
$R^2$ is selected from the group consisting of $C_1$-$C_{20}$ alkylene;
FG is a functional group independently selected from OH and $N(R^1)H$;
P is a polymeric group having a $M_n$ of about 250 to about 50,000;
$R^5$ is selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups may be interrupted by 1-5 heteroatoms selected from the group consisting of O, N and S; and
$R^6$ is selected from the group consisting of $C_2$-$C_{20}$ alkylene.
The present invention further relates to biodegradable biomedical articles comprising the supramolecular biodegradable polymer.

DETAILED DESCRIPTION OF THE INVENTION

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

(Self)-complementary units capable of forming at least four hydrogen bonds form in principle non-covalent moieties with each other. When the (self)-complementary units are capable of forming four hydrogen bonds in a row, they are used in their abbreviated form "4H-unit". However, it is within the scope of this invention that the (self)-complementary units (including the 4H-units) can form non-covalent moieties with other materials capable of forming less than four hydrogen bonds. Units capable of forming at least four hydrogen bonds can form a non-self-complementary or a self-complementary binding group. Non-self-complementary means for example that a 4H-unit (I) forms a bonding moiety (I)-(II) with a unit (II), wherein (II) is a different 4H-unit. Self-complementary means that two 4H-units (I) form a bonding moiety (I)-(I). It is preferred that the 4H-unit is self-complementary. The units according to Formulas (1), (2), (3) and (4) and the units according to Formulas (5) and (6) form, when incorporated in the supramolecular biodegradable polymer according to the present invention, (self)-complementary units.

Since the term "(self)-complementary units capable of forming four hydrogen bonds in a row is used in its abbreviated form "4H-unit", a "supramolecular polymer comprising a (self-)complementary unit capable of forming at least four hydrogen bonds in a row" is in this document alternatively indicated as a "supramolecular polymer comprising a 4H-unit". The 4H-unit is covalently attached to or covalently incorporated in the polymer chain.

The term "biodegradable" when used in this document relates to cell-mediated degradation, enzymatic degradation, hydrolytic degradation of the supramolecular biodegradable polymer and/or the biodegradable biomedical article comprising the supramolecular biodegradable polymer. The term "biodegradable" may also relate to elimination of the supramolecular biodegradable polymer and/or the biodegradable biomedical article comprising the supramolecular biodegradable polymer from living tissue.

In structural units F and G, the 2-position is substituted by a urea moiety so that they form a 4H-unit as is shown below for Formula (1) and for Formula (5):

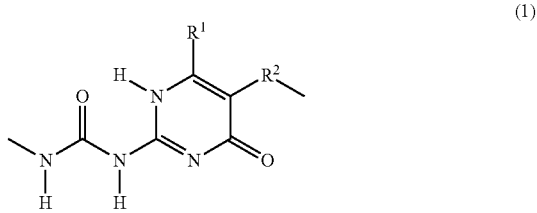

(1)

-continued (5)

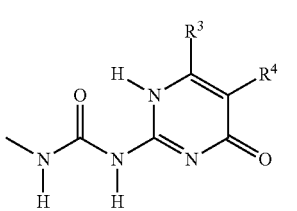

The term "room temperature" as used in this document has its normal meaning, i.e. that it indicates a temperature in the range of about 20° C. to about 25° C.

Molecular weights such as $M_n$ are expressed as g/mol.

General Definitions

An urea moiety as indicated in this document is to be understood as a moiety according to the formula:

—NR—C(X)—NR— wherein X is O or S, preferably O; and wherein R is, independently, a hydrogen atom or a linear alkyl group, preferably a hydrogen atom.

An amide moiety as indicated in this document is to be understood as a moiety according to the formula:

—NR—C(X)— wherein X and R are as described above.

An urethane moiety as indicated in this document is to be understood as a moiety according to the formula:

—NR—C(X)—X— wherein X and R are as described above (X can independently be O or S).

An ester moiety as indicated in this document is to be understood as a moiety according to the formula:

—C(X)—X— wherein X is as described above (X can independently be O or S).

A carbonate moiety as indicated in this document is to be understood as a moiety according to the formula:

—X—C(X)—X— wherein X is as described above (X can independently be O or S).

An amine moiety as indicated in this document is to be understood as a moiety according to the formula:

—NR$_2$— wherein R is as described above.

An ether moiety as indicated in this document is to be understood as a moiety according to the formula:

—X— wherein X is as described above.

An isocyanate group is to be understood as a —NCX group, wherein X is as described above.

The Supramolecular Biodegradable Polymer

The supramolecular biodegradable polymer has preferably a number average molecular weight $M_n$ of about 1,200 to about 1,000,000, more preferably about 4,000 to about 100,000, even more preferably about 8,000 to about 60,000, yet even more preferably about 10,000 to about 40,000, and most preferably about 10,000 to about 30,000 Dalton.

The supramolecular biodegradable polymer may be a random polymer in which the structural units A, B, C and F occur in different random sequences. The supramolecular biodegradable polymer may also be a segmented polymer in which regular sequences of A, B, C and F units can be found as can for example schematically be shown as:

—C-A-C—F—C-A-C—B—C—B— or

—C—F—C-A-C—F—C—B—.

The supramolecular biodegradable polymer may also be a random polymer in which the structural units A, B and C occur in different random sequences, wherein the supramolecular biodegradable polymer is end-capped with structural unit G.

In a preferred embodiment, a 9% w/v solution of the supramolecular biodegradable polymer in a mixture of chloroform and methanol (10/1 v/v) has a dynamic viscosity at 25° C. of about 0.5 to about 10 Pa·s, preferably of about 0.8 to about 8 Pa·s, most preferably of about 0.8 to about 5 Pa·s, as measured with a rotational viscometer.

In another preferred embodiment of this invention, the supramolecular biodegradable polymer absorbs less than about 50% by weight of water, based on the total weight of the supramolecular biodegradable polymer, when soaked into excess of water at 25° C. for about one hour.

The supramolecular biodegradable polymer according to the present invention has a high mechanical strength and a high elasticity and is very suitable for biomedical applications. Therefore, the supramolecular biodegradable polymer according to the present invention has preferably a Young's modulus of at least 10 MPa, preferably at least 20 MPa, an even more preferably of at least 40 MPa, as determined by standard test method ASTM D 1708-96 at room temperature, with a crosshead speed of 20 mm/min. Preferably, the Young's modulus is lower than 150 MPa, preferably lower than 80 MPa, most preferably lower than 60 MPa.

The supramolecular biodegradable polymer according to the present invention has preferably also a modulus at 100% elongation of at least 5 MPa, more preferably at least 10 MPa, as determined by standard test method ASTM D 1708-96 at room temperature, with a crosshead speed of 20 mm/min. Moreover, the supramolecular biodegradable polymer is not yielding which means in this application that the modulus at 30% elongation is at least 1.0 times the modulus at 10% elongation, preferably at least 1.2 times the modulus at 10% elongation, and most preferably at least 1.4 times the modulus at 10% elongation, according to test method ASTM D 1708-96 at room temperature, with a crosshead speed of 20 mm/min.

The supramolecular biodegradable polymer according to the present invention has preferably also an elongation at break of at least 100%, more preferably of at least 200%, and most preferably of at least 300%, according to standard test method ASTM D 1708-96 at room temperature, with a crosshead speed of 20 mm/min.

The supramolecular biodegradable polymer according to the present invention has preferably at least two thermal transitions selected from a glass transition or a melting point at a temperature between about 40° and about 140° C., more preferably between about 50° and about 130° C.

Process for Preparing the Supramolecular Biodegradable Polymer

The present invention also relates to a process for preparing the supramolecular biodegradable polymer. In this process, a compound F' that is independently selected from the group consisting of Formulas (7), (8), (9) and (10), or a mixture thereof:

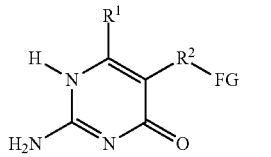
(7)

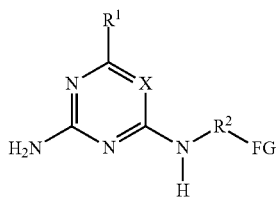
(8)

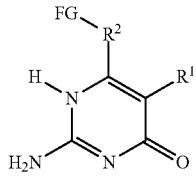
(9)

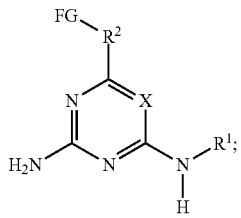
(10)

or
a compound G' that is independently selected from the group consisting of Formulas (11) and (12), or a mixture thereof:

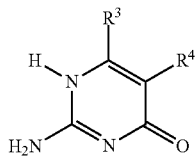
(11)

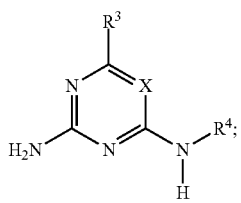
(12)

is reacted with:
a diisocyanate compound C' according to the Formula OCN—$R^6$—NCO;
a polymer A' according to the Formula FG-P-FG; and
a compound B' according to the Formula FG-$R^5$-FG;
wherein:
X is N or $CR^1$;
$R^1$, $R^3$, and $R^4$ are independently selected from the group consisting of:

(a) hydrogen;
(b) $C_1$-$C_{20}$ alkyl;
$R^2$ is selected from the group consisting of $C_1$-$C_{20}$ alkylene;
FG is a functional group independently selected from OH and $N(R^1)H$;
P is a polymeric group having a $M_n$ of about 250 to about 50,000;
$R^5$ is selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups may be interrupted by 1-5 heteroatoms selected from the group consisting of O, N and S; and
$R^6$ is selected from the group consisting of $C_2$-$C_{20}$ alkylene.

Accordingly, in the process according to the invention, components A', B', C' and F' or components A', B', C' and G' can be reacted as a mixture. In this process, it is preferred that the ratio of the molar amounts of components A', B', C' and F' are ranging from about 1:1:3:1 to 1:6:8:1, more preferably ranging from about 1:2:4:1 to 1:3:5:1, most preferably about 1:2:4:1, in which the molar amount of C' is always equal to about 0.8 to about 1.2 times the total molar amount of A' plus B' plus F', and that the ratio of the molar amounts of components A', B', C' and G' are about ranging from about 10:10:21:2 to 20:20:41:2, more preferably ranging from about 14:14:29:2 to 18:18:37:2, most preferably about 16:16:33:2, in which the molar amount of C' is always equal to about 0.8 to about 1.2 times the total molar amount of A' plus B' plus half the molar amount of G'. However, according to the invention it is also possible to react the components A', B', C' and F' or components A', B', C' and G' in distinct steps as is explained below. These variants consisting of two or more distinct reaction steps are within the scope of the present invention.

It is further within the scope of the invention that the molar amounts may differ from unity by about ±0.2, e.g. when components A', B', C' and F' are reacted as a 1:2:4:1 mixture, the molar amounts in the mixture of component A' and component F' may be within in the range of about 0.8 to about 1.2, the molar amount of component B' may be within the range of about 1.8 to about 2.2, and the molar amount of component C' may be within the range of about 3.8 to about 4.2. Likewise, when components A', B', C' and G' are reacted as a 16:16:33:2 mixture, the molar amounts in the mixture of component A' and component B' may be within in the range of about 15.8 to about 16.2, the molar amount of component C' may be within the range of about 32.8 to about 33.2, and the molar amount of component G' may be within the range of about 1.8 to about 2.2.

According to the invention, it is preferred that the molar amounts differ from unity by not more than about +0.1, more preferably not more than about ±0.05.

Without being bound by theory, it is believed that the major course of the reactions are as schematically shown in Scheme 1 and Scheme 2, wherein components F' according to Formulas (7)-(10) are schematically shown as $H_2N$—F'''—OH (which means that in this example FG represents OH) and components G' are schematically shown as $H_2N$-G'''.

Scheme 1

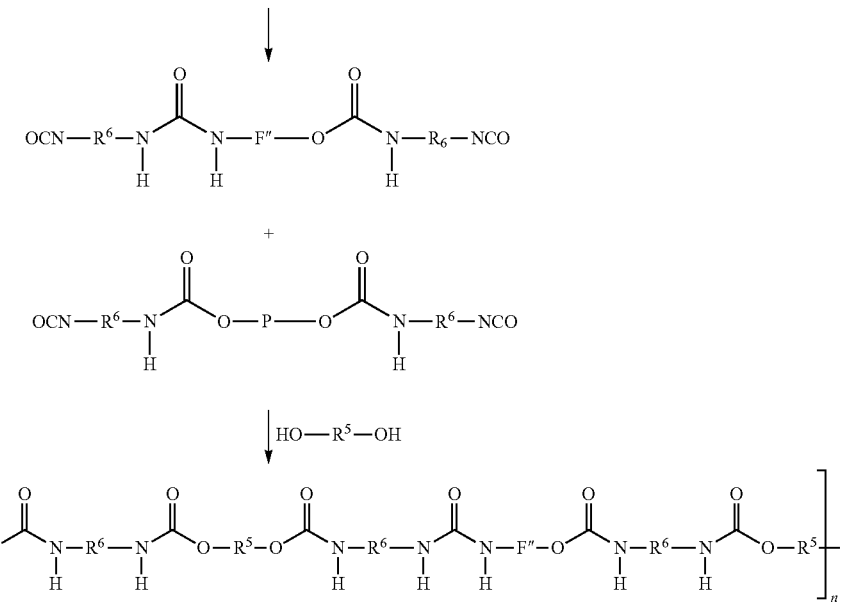

wherein n is such that the number average molecular weight $M_n$ is about 1,200 to about 1,000,000.

It is preferred that n is in the range of about 6 to about 20, more preferably about 10 to about 18.

potentially unreacted C' are reacted with component B' to form the supramolecular biodegradable polymer. According to this embodiment, it is preferred that prepolymer P1 and functionalised component F' are reacted with component B'

Scheme 2

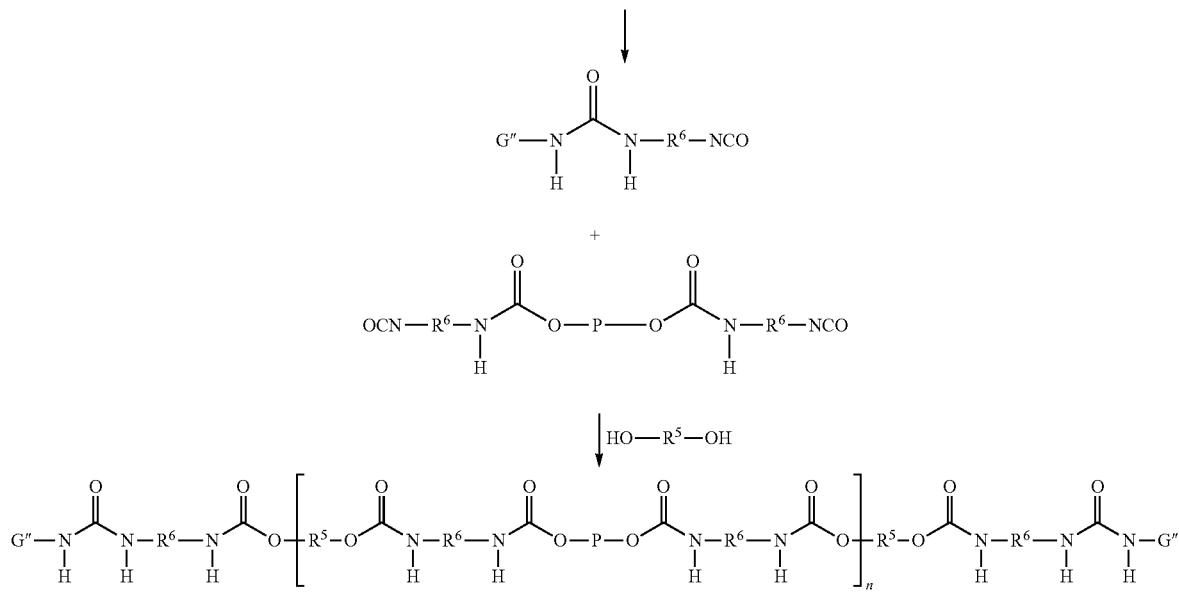

As a first preferred alternative, components A', C' and F' are reacted in a first step thereby forming a prepolymer P1 and a functionalised component F' (Scheme 1), where after prepolymer P1 and the functionalised component F' and wherein the ratio of the molar amounts of prepolymer P1, and functionalised component F' to component B' is in between 1:1:1 and 1:1:6, and wherein the molar amounts may differ from unity by about ±0.2. Likewise, components A', C' and G' are reacted in a first step thereby forming a prepolymer P1 and a functionalised component G' (Scheme 2), where after prepolymer P1 and the functionalised component G' are reacted with component B' to form the supramolecular biodegradable polymer wherein the ratio of the molar amounts of prepolymer P1, and functionalised component G' to component B' is in between 10:10:2 and 20:20:2, and wherein the molar amounts may differ from unity by about ±0.2.

Accordingly, the present invention also relates to a process for preparing the supramolecular biodegradable polymer, wherein:

a compound F' that is independently selected from the group consisting of Formulas (7), (8), (9) and (10), or a mixture thereof;

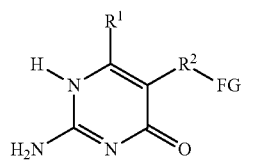
(7)

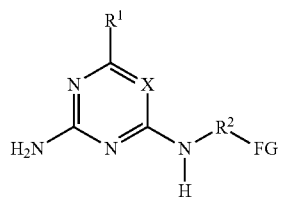
(8)

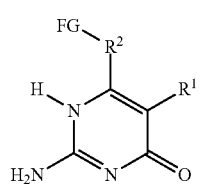
(9)

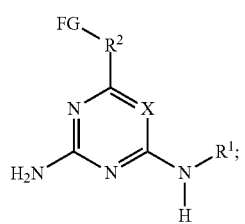
(10)

or
a compound G' that is independently selected from the group consisting of Formulas (11) and (12), or a mixture thereof:

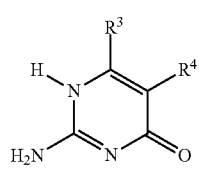
(11)

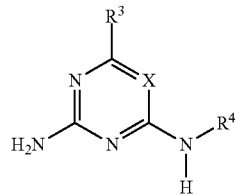
(12)

is reacted in a first step with a diisocyanate compound C' according to the Formula OCN—$R^6$—NCO and a polymer A' according to the Formula FG-P-FG to form a prepolymer P1 and a functionalised component F';

wherein in a second step the prepolymer P1 and the functionalised component F' are reacted with a compound B' according to the Formula FG-$R^5$-FG;

wherein:

X is N or $CR^1$;

$R^1$, $R^3$, and $R^4$ are independently selected from the group consisting of:

(a) hydrogen;

(b) $C_1$-$C_{20}$ alkyl;

$R^2$ is selected from the group consisting of $C_1$-$C_{20}$ alkylene;

FG is a functional group independently selected from OH and $N(R^1)H$;

P is a polymeric group having a $M_n$ of about 250 to about 50,000;

$R^5$ is selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups may be interrupted by 1-5 heteroatoms selected from the group consisting of O, N and S; and $R^6$ is selected from the group consisting of $C_2$-$C_{20}$ alkylene.

As another alternative, components A' and C' and components F' and C' are reacted separately to form a prepolymer P1 and a functionalised component F', where after prepolymer P1 and functionalised component F' are combined and reacted with 2-6 molar equivalents of component B' and additional 0-4 molar equivalents of C' (Scheme 3). According to this alternative, components A' and C' and components F' and C' are reacted in a molar ratio of preferably 1:2, respectively, wherein the molar amounts may differ from unity by about ±0.2. Prepolymer P1 and functionalised component F' are then reacted with 2-6 molar equivalents of component B', and 0-4 molar equivalents of component C'. Again, the molar amounts may differ from unity by about ±0.2.

According to yet another alternative, component B' is reacted with component C' to form a functionalised component B', wherein the latter is reacted with prepolymer P1 (which is formed in a separate step) and component F' or with prepolymer P1 (which is formed in a separate step) and component G'.

According to yet another alternative, component B' is reacted with component C' to form a functionalised component B', wherein the latter is reacted with component A' and functionalised component F' (which is formed in a separate step) or with component A' and functionalised component G' (which is formed in a separate step).

These alternative processes are depicted in Schemes 3, 4 and 5.

Scheme 3
 
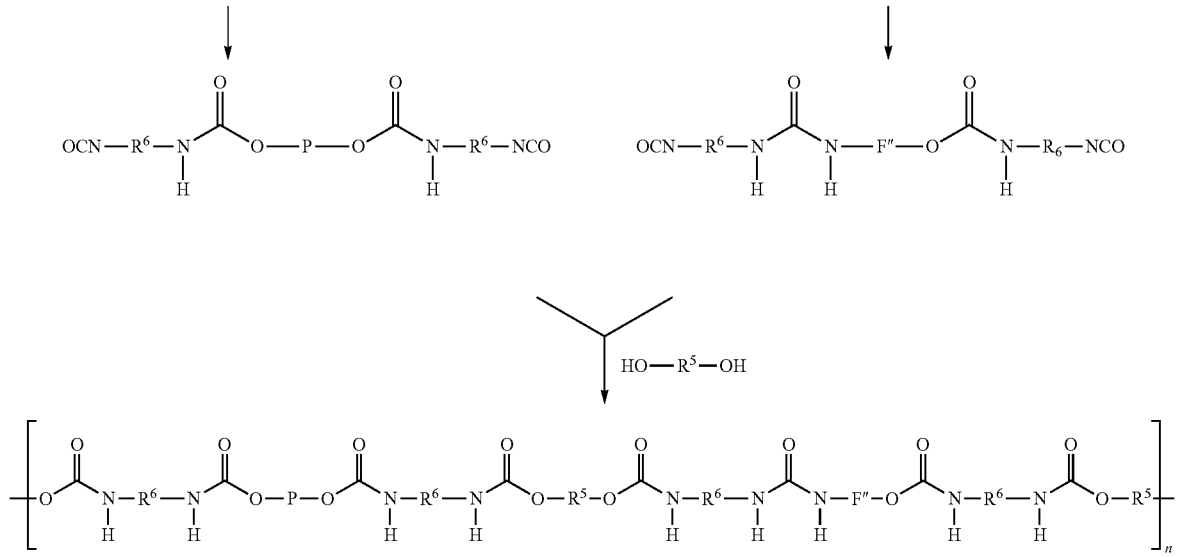
Scheme 4
 
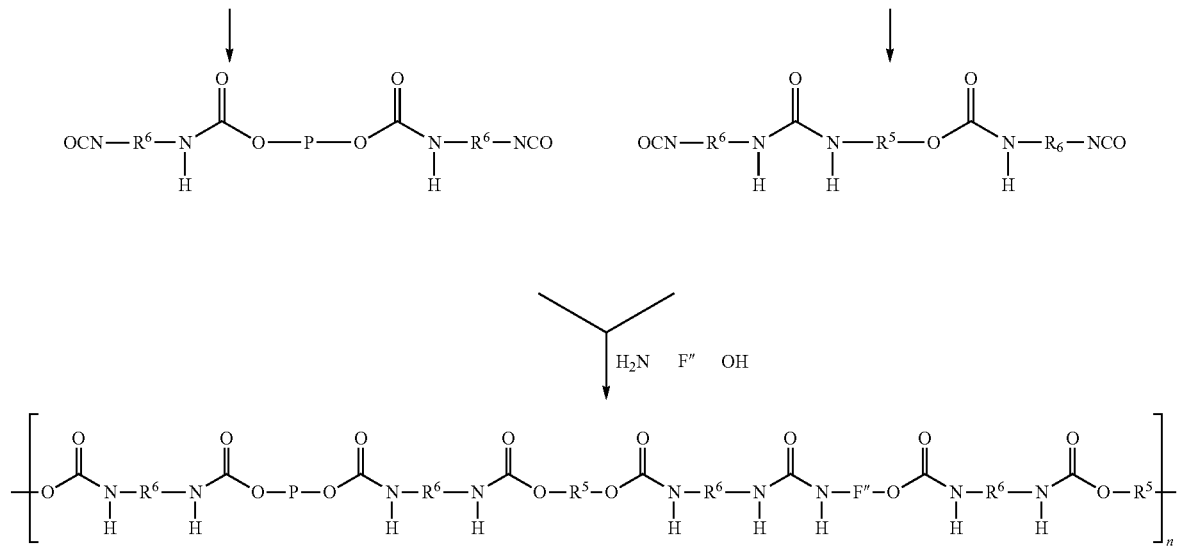
Scheme 5
 

-continued

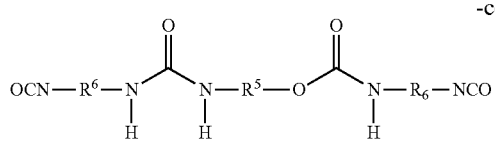
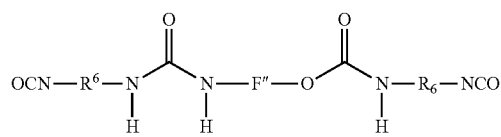

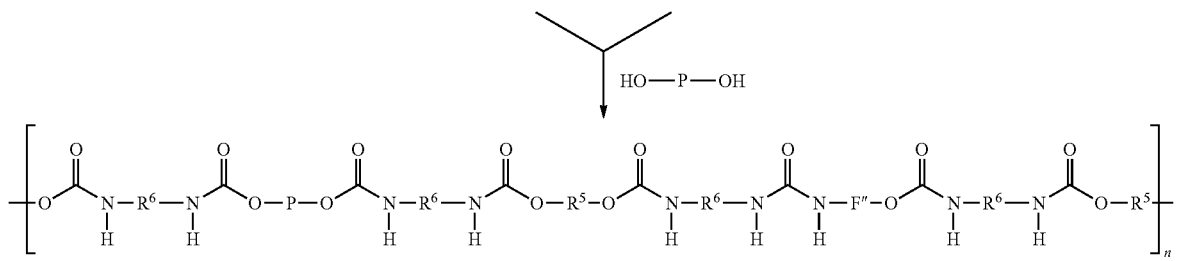

Diisocyanate compound C'

The diisocyanate compound C' has the Formula OCN—$R^6$—NCO, wherein $R^6$ is preferably selected from the group consisting of cyclic, linear or branched $C_2$-$C_{20}$ alkylene groups. More preferably, $R^6$ is selected from the group consisting of linear $C_2$-$C_{20}$ alkylene groups, most preferably linear $C_2$-$C_{16}$ alkylene groups.

The diisocyanate compound C' is more preferably selected from the group consisting of methylene dicyclohexane 4,4-diisocyanate (HMDI), isophorone diisocyanate (IPDI), hexane diisocyanate (HDI), uretdione dimers of HDI, 1,6-diisocyanato-2,2,4-trimethylhexane and 1,6-diisocyanato-2,4,4-trimethylhexane. More preferably, the diisocyanate compound C' is hexane diisocyanate (HDI) or methylene dicyclohexane 4,4-diisocyanate (HMDI). The diisocyanate compound C' is most preferably hexane diisocyanate (HDI).

Polymer A'

The polymer A' has the Formula FG-P-FG, wherein P is preferably a polymeric group having a number average molecular weight $M_n$ of about 250 to about 50,000, more preferably about 400 to about 20,000, even more preferably about 600 to about 2,500, yet even more preferably about 600 to about 1,500 and most preferably about 600 to about 1,000 g/mol.

The polymer A' is preferably telechelic. Whereas the Formula FG-P-FG indicates that polymer A' is exactly bifunctional, in practice this telechelic polymer can better be represented as P-(FG)$_w$ wherein w may vary within the range of about 1.8 to about 2, more preferably about 1.9 to about 2 and most preferably about 1.95 to about 2.

The polymer A' is preferably a linear polymer.

It is furthermore preferred that FG represents OH.

The polymer A' can be selected from the group consisting of biodegradable polymer backbones. Most preferably, the polymer A' is hydroxy terminated which implies that FG represents OH.

Preferably, polymer A' is a hydrophobic polymer. Hydrophobic polymers A' are preferred in order to prevent that the biodegradation is too fast in the aqueous environment that constitutes living tissue. According to this invention, a hydrophobic polymer is defined as a polymer having a solubility in water at 25° C. that is lower than 10 g/L, more preferably lower than 1 g/L, and/or a polymer having a water contact angle higher than 50° as measured at 25° C. using a static sessile drop method, more preferably higher than 55°, and most preferably higher than 70°.

The polymer A' is preferably selected from the group consisting of polyethers, polyesters, polyorthoesters, polyamides, polypeptides, polyacrylates, polymethacrylates, polycarbonates and co-polymers of such polymers. More preferably, the polymer A' is selected from the group consisting of polyethers, polyesters, polycarbonates, polyorthoesters, polypeptides and co-polymers of such polymers. More preferably, the polymer A' is selected from the group consisting of polycarbonates, polyesters, polyethers and copolymers of such polymers.

In one specific embodiment of this invention, the polymer A' is selected from the group consisting of polycarbonates, polyesters, and copolymers of such polymers. Most preferably, the polymer A' is a polyester or a copolymer of a polyester (copolyester).

In another specific embodiment of this invention, the polymer A' is selected from the group consisting of polyethers, most preferably polyethylene glycols.

Preferred polyesters and copolyesters are selected from polyesters and copolyesters made by polycondensation of dicarboxylic acids and diols, by polycondensation of hydroxyacids, or by ringopening (co)polymerisation of appropriate monomers which are preferably selected from the group consisting of ε-caprolactone, glycolide, (L)-lactide, (D)-lactide, 6-valerolactone, 1,4-dioxane-2-one, 1,5-dioxepan-2-one and oxepan-2,7-dione. Preferred polyesters and copolyesters are preferably poly ε-caprolactonediols, hydroxy terminated polyadipates and hydroxy terminated polyglutarates. A preferred group of hydroxy terminated polyesters and copolyesters consists of poly ε-caprolactonediols, hydroxy terminated poly(1,4-butylene adipate)s, hydroxy terminated poly(1,2-ethylene adipate)s, hydroxy terminated poly(1,4-butylene glutarate)s, hydroxy terminated poly(2-methyl-1,3-propylene adipate)s, hydroxy terminated poly(2-methyl-1,3-propylene glutarate)s, hydroxy terminated poly(2-methyl-1,5-pentylene adipate)s, polyesterdiols of polylactides, polyglycolides, poly(lactide-co-glycolide)s, poly(hydroxy butyrate)s, polyterephthalates such as polyethyleneterephthalates and polybutyleneterephthalates, polyisophthalates, polyphthalates, and polyesters derived from dimerised fatty acids, such as the different Priplast grades (p.e. Priplast 3190 or Priplast 3192) marketed by Croda, UK. More preferably, the hydroxy terminated polyesters and copolyesters are selected from the group consisting of hydroxy terminated polyesters or copolyesters made by ringopening polymerisation of lactone and/or lactides, polyesters from dimerized fatty acids, poly (ε-caprolactone), poly(D,L-lactide), poly(L-lactide), or their copolyesters, even more preferably poly(ε-caprolactone) or poly(caprolactone-co-L-lactide), most preferably poly(ε-caprolacton).

Polycarbonates are preferably selected from hydroxy terminated polycarbonates and copolycarbonates based on alkyldiol polycarbonate and polycarbonates and copolycarbonates made by ringopening polymerization of trimethylenecarbonate, 1,3-dioxepane-2-one, 1,3-dioxanone-2-one, and 1,3,8,10-tetraoxacyclotetradecane-2,9-dione. More preferably, polycarbonates are selected from alkyldiol polycarbonate, most preferably 1,6-hexanediol polycarbonate.

Polyethers are preferably selected from polyethylene glycols, polypropylene glycols, poly(ethylene-co-propylene) glycols (random or block), poly(ethylene-block-propylene-block-ethylene) glycols (also known as Pluronics®), polytetramethylene glycols (i.e. poly-tetrahydrofurans) and poly (ethylene-co-tetramethylene) glycols, and their copolyethers. More preferably, polyethers are selected from the group consisting of polyethylene glycol and poly(tetrahydrofuran). Most preferably, the polyether is a polyethylene glycol.

Compound B'

The compound B' has the Formula FG-$R^5$-FG, wherein $R^5$ is preferably selected from the group consisting of $C_2$-$C_{44}$ alkylene, $C_6$-$C_{44}$ arylene, $C_7$-$C_{44}$ alkarylene and $C_7$-$C_{44}$ arylalkylene, wherein the alkylene groups, arylene groups, alkarylene groups and arylalkylene groups may be interrupted by 1-5 heteroatoms selected from the group consisting of O, N and S.

Preferably, $R^5$ is selected from $C_2$-$C_{44}$ alkylene, more preferably $C_2$-$C_{12}$ alkylene, even more preferably $C_4$-$C_{12}$ alkylene, wherein the alkylene group is optionally interrupted with one or more, preferably 1-5, oxygen or nitrogen atoms.

The alkylene groups may be linear, cyclic or branched. Preferably, the alkylene group is linear.

The compound B' has preferably a molecular weight of about 56 to about 600 g/mol, more preferably a molecular weight of about 90 to about 210 g/mol, most preferably a molecular weight of about 100 to about 180 g/mol.

Preferably, the compound B' is a diol, more preferably a linear $C_2$-$C_{20}$ alkyl α,ω-diol, wherein the alkylene group is optionally interrupted with one or more, preferably 1-5, oxygen atoms. Even more preferably the compound B' is selected from diethylene glycol, triethyleneglycol, and 1,6-hexanediol. Most preferably, the compound B' is 1,6-hexanediol.

The Process

The process for the preparation of the supramolecular biodegradable polymer according to this invention can be done by any method known in the art, for example in solution or in the bulk using reactive extrusion. The process is preferably performed at a temperature between about 10° C. and about 140° C., more preferably between about 20° C. and about 120° C., and most preferably between about 40° C. and about 90° C.

The process for the preparation of the supramolecular biodegradable polymer may be performed in the presence of a catalyst. Examples of suitable catalysts are known in the art and they promote the reaction between isocyanates and hydroxyl groups. Preferred catalysts include tertiary amines and catalysts comprising a metal. Preferred tertiary amines are 1,4-diazabicyclo[2.2.2]octane (DABCO) and 1,8-diazabicyclo[5.4.0]undec-7-ene (DBU). Preferred catalysts comprising a metal are tin(IV) compounds and zirconium (IV) compounds, preferably selected from the group consisting of tin(II)octanoate, dibutyltin(IV)laurate and zirconium(IV)acetoacetate. Most preferably, the catalyst is tin(II) octanoate. The amount of catalyst is generally below about 1% by weight, preferably below about 0.2% by weight and most preferably below about 0.03% by weight, based on the total amount of reactants.

In a preferred embodiment of this invention, the process is performed in the presence of a non-reactive organic solvent, wherein it is preferred that the amount of the non-reactive organic solvent is at least about 20 weight %, more preferably at least about 40 weight %, even more preferably at least about 60 weight %, and most preferably at least about 70 weight %, based on the total weight of the reaction mixture. It is also preferred that the reaction mixture does not comprise any inorganic solvents such as water. Non-reactive solvents are preferably selected from non-protic polar organic solvents, preferably tetrahydrofuran, dioxane, N-methylpyrollidone, dimethylformamide, dimethylacetamide, dimethyl sulfoxide, propylene carbonate, ethylene carbonate, 2-methoxy-ethyl-acetate. Most preferably, the non-reactive solvent is dimethyl sulfoxide or propylene carbonate.

The supramolecular biodegradable polymer can be isolated as such, or can be isolated as a powder after precipitation in a non solvent, chopped into pellets, spun in fibers, extruded into films, directly dissolved in a medium of choice, or transformed or formulated into whatever form that is desired.

Preferably, the supramolecular biodegradable polymer is molten and melt-spun, extruded with fused deposition modelling, processed with another 3D printing techniques such as laser sintering, or dissolved in a volatile organic solvent and electrospun, in order to obtain a scaffold for tissue engineering. Said scaffold may comprise woven or non-woven fibers. Most preferably, the supramolecular biodegradable polymer is electrospun from solution into a scaffold for tissue engineering comprising non-woven fibers.

Applications

The supramolecular biodegradable polymers according to the invention are preferably suitable for manufacturing biomedical articles, in particular medical implants, scaffolds for tissue engineering, in which human or animal tissue is grown on a substrate, scaffolds for cardio-vascular applications, such as artificial heart valves or vascular grafts, or ligaments reconstructions, but are not limited thereto (they could also be all kinds of scaffolds used for other organs/devices/objects).

EXAMPLES

The following examples further illustrate the preferred embodiments of the invention. When not specifically mentioned, chemicals are obtained from Aldrich.

Example 1: Preparation of UPy-Monomer A

2-Acetylbutyrolactone (2.38 g, 19 mmol) and guanidine carbonate (3.3 g, 37 mmol) were put to reflux in absolute ethanol (20 mL) in the presence of triethylamine (5.2 mL). The solution became yellow and turbid. After overnight heating at reflux, the solid was filtered, washed with ethanol, and suspended in water. The pH was adjusted to a value of 6-7 with an HCl-solution, and the mixture was stirred for a while. Filtration, rinsing of the residue with water and ethanol and subsequent drying of the solid gave the pure UPy-monomer A. $^1$H NMR (400 MHz, DMSO-D): δ 11.2 (1H), 6.6 (2H), 4.5 (1H), 3.4 (2H), 2.5 (2H), 2.1 (3H). FT-IR (neat): ν (cm$^{-1}$) 3333, ☐3073, 2871, 1639, 1609, 1541, 1487, 1393, 1233, 1051, 915, 853, 789, 716.

Example 2: Preparation of UPy-Monomer B

UPy-monomer A (1 g, 5.9 mmol) was suspended in 1,6-hexyldiisocyanate (12 mL, 75 mmol) and pyridine (1 mL) and was stirred at 90° C. A clear solution developed, and thereafter some gel particles formed (unwanted). The solution was cooled and filtered through some celite. The filtrate was dropped into pentane giving a white precipitate. This precipitate was again stirred in pentane to remove the last traces of 1,6-hexyldiisocyanate. Isolation via filtration was followed by drying, giving the pure diisocyanate. $^1$H NMR (400 MHz, CDCl$_3$): δ 13.1 (1H), 11.9 (1H), 10.2 (1H), 4.8-4.6 (1H), 4.2 (2H), 3.3 (6H), 3.1 (2H), 2.7 (2H), 2.3 (3H), 1.7-1.2 (16H). FT-IR (neat): ν (cm$^{-1}$) 3314, ☐2936, 2263, 1688, 1662, 1640, 1590, 1535, 1444, 1257, 1140, 1025, 780, 742.

Example 3: Preparation of Polymer 1

Telechelic hydroxy terminated polycaprolacton with a molecular weight of 1250 Da (20.4 g, 16.3 mmol, dried in vacuo), UPy-monomer B (8.24 g, 16.3 mmol), hexamethylene diisocyanate (5.48 g, 32.6 mmol) and one drop of tin dioctoate were dissolved in dry DMSO (60 mL) and stirred at 80° C. The next day, 1,6-hexanediol (3.85 g, 32.6 mmol, dried in vacuo) was added to the reaction mixture, followed by stirring for another 2 hours at 80° C. The reaction mixture was cooled to 25° C. and its viscosity was lowered by the addition of additional DMSO in order to precipitate the mixture in water. The polymer was collected as a white elastic solid, redissolved in chloroform/methanol (7/3 v/v) and repriciptated in an excess of methanol. This resulted in a clear elastic solid after drying in vacuo at 50° C. SEC (THF, PS-standards): $M_n$=14.6 kDa, Đ=1.8.

Example 4: Preparation of Polymer 2

Telechelic hydroxy terminated polycaprolacton with a molecular weight of 2000 Da (40.8 g, 20.4 mmol, dried in vacuo) and hexamethylene diisocyanate (13.7 g, 81.6 mmol) were stirred together at 80° C. in the presence of one drop of tin dioctoate for 2 hours. To this reaction mixture was subsequently added UPy-monomer A (3.45 g, 20.4 mmol) dissolved in dry DMSO (120 mL) and stirred overnight at 80° C. The next day, 1,6-hexanediol (4.81 g, 40.8 mmol, dried in vacuo) was added to the reaction mixture, followed by stirring for another 2 hours at 80° C. The reaction mixture was cooled to 25° C. and its viscosity was lowered by the addition of additional DMSO in order to precipitate the mixture in water. The polymer was collected as a white elastic solid, redissolved in chloroform/methanol (7/3 v/v) and repriciptated in an excess of methanol. This resulted in a clear elastic solid after drying in vacuo at 50° C. SEC (THF, PS-standards): $M_n$=26 kD, Đ=1.4.

Example 5: Preparation of Polymer 3

Telechelic hydroxy terminated polycaprolacton with a molecular weight of 2000 Da (40.0 g, 20 mmol, dried in vacuo) and hexamethylene diisocyanate (16.5 g, 98 mmol) were stirred together at 80° C. in the presence of one drop of tin dioctoate for 2 hours. To this reaction mixture was subsequently added UPy-monomer A (3.38 g, 20 mmol) dissolved in dry DMSO (120 mL) and stirred overnight at 80° C. The next day, 1,6-hexanediol (7.08 g, 60 mmol, dried in vacuo) was added to the reaction mixture, followed by stirring for another 2 hours at 80° C. The reaction mixture was cooled to 25° C. and its viscosity was lowered by the addition of additional DMSO in order to precipitate the mixture in water. The polymer was collected as white elastic solid, redissolved in chloroform/methanol (7/3 v/v) and reprecipitated in an excess methanol. This resulted in a clear elastic solid after drying in vacuo at 50° C. SEC (THF, PS-standards): $M_n$=21 kDa, Đ=1.5.

Example 6: Preparation of Polymer 4

Telechelic hydroxy terminated polycaprolacton with a molecular weight of 800 Da (40.0 g, 50 mmol, dried in vacuo), 1,6-hexanediol (11.7 g, 99 mmol), and UPy-monomer A (8.36 g, 49 mmol) were dissolved in dry DMSO (120 mL) at 80° C. To this reaction mixture was added hexamethylene diisocyanate (32.6 g, 19 mmol) while stirring, followed by the addition of one drop of tin dioctoate. This reaction mixture was stirred overnight at 80° C. The next day, the reaction mixture was cooled to 25° C. and its viscosity was lowered by the addition of additional DMSO in order to precipitate the mixture in water. The polymer was collected as white elastic solid, redissolved in chloroform/methanol (7/3 v/v) and reprecipitated in an excess methanol. This resulted in a clear elastic solid after drying in vacuo at 50° C. SEC (THF, PS-standards): $M_n$=16 kDa, Đ=1.4.

Example 7: Preparation of Polymer 5

Telechelic hydroxy terminated poly(ethylene glycol) with a molecular weight of 3 kDa (20 gram, 6.67 mmol) was dried at 120° C. in vacuo for 2 hours. Subsequently, UPy-monomer A (1.13 gram, 6.67 mmol), hexanediisocyanate (4.13 gram, 24.6 mmol), 50 mL dimethylformamide and one drop of dibutyltindilaurate were added to the polymer. The reaction mixture was stirred at 90° C. After one hour, 1,6-hexanediol (1.56 gram, 13.3 mmol) was added. The reaction mixture was stirred for 8 hours at 90° C. Subsequently, the reaction mixture was diluted with 50 mL of methanol and poured into 500 mL of diethylether. The precipitated polymer was dissolved into 70 mL chloroform and 70 mL methanol and poured into 500 mL diethylether. The precipitated polymer was dried in vacuo and obtained as a white solid. SEC (DMF/LiBr, PS-standards): $M_n$=27 kDa, Đ=3.0.

Example 8: Preparation of Polymer 6

Telechelic hydroxy terminated poly(ethylene glycol) with a molecular weight of 10 kDa (20 gram, 2 mmol) was dried at 120° C. in vacuo for 2 hours. Subsequently, UPy-monomer A (0.34 gram, 2 mmol), hexanediisocyanate (1.24 gram, 7.38 mmol), 50 mL dimethylformamide and one drop of dibutyltindilaurate were added to the polymer. The reaction mixture was stirred at 90° C. After one hour, 1,6-hexanediol (0.47 gram, 4 mmol) was added. The reaction mixture was stirred for 8 hours at 90° C. Subsequently, the reaction mixture was diluted with 50 mL of methanol and poured into 500 mL of diethylether. The precipitated polymer was dissolved into 70 mL chloroform and 70 mL methanol and poured into 500 mL diethylether. The precipitated polymer was dried in vacuo and obtained as a white solid. SEC (DMF/LiBr, PS-standards): $M_n$=55 kDa, D=1.9.

Comparative Example 1: Preparation of Polymer C1

Telechelic hydroxy terminated polycaprolacton with a molecular weight of 2000 Da (73.0 g, 37 mmol, dried in vacuo) was stirred together with UPy-monomer A (5.29 g, 31 mmol) at 60° C. To this reaction mixture was added isophoronene diisocyanate (16.2 g, 73 mmol) and dibutyltin-dilaurate (15 mg) while stirring, followed by stirring the reaction mixture for 8 hours at 80° C. and subsequent 1.5 hours at 120° C. Subsequent the reaction mixture was put in an oven at 150° C. for 1 hour, followed by cooling to 25° C. and soaking the polymer in ethanol overnight. The polymer was dried in vacuo at 50° C., resulting in a tough opaque material. SEC (THF, PS-standards): $M_n$=14.6 kDa, D=1.8.

Comparative Example 2: Preparation of Polymer C2

Telechelic hydroxy terminated polycaprolacton with a molecular weight of 2100 Da (25.0 g, 12 mmol, dried in vacuo) was dissolved in dry chloroform (750 mL) after which 2(6-isocyanatohexylaminocarbonylamino)-6-methyl-4[1H]pyrimidinone (8.8 g, 30 mmol, obtained according to Folmer et al., Adv. Mater. 12, 874, 2012) was added. After addition of one drop of dibutyltindilaurate the solution was refluxed for 16 hours. Then 5 gram silica kieselgel 60 were added and the mixture was refluxed for another 8 hours. After dilution of the mixture with chloroform, the silica was removed by filtration using hyflo. The solution was concentrated under reduced pressure. The material was precipitated from chloroform in hexane and filtrated. The resulting material was dried for 24 hours in vacuo resulting in a white fluffy material. SEC (THF, PS-standards): $M_n$=1.7 kDa, D=1.3.

Comparative Example 3: Preparation of Polymer C3

Comparative Example 3 is similar to Example 4, wherein instead of hexamethylene diisocyanate (HDI), isophoron diisocyanate (IPDI) was used.

Telechelic hydroxy terminated polycaprolacton with a molecular weight of 808 Da (10.0 g, 12.4 mmol), 1,6-hexanediol (2.92 g, 24.8 mmol) and UPy-monomer A (2.09 g, 12.4 mmol) were dissolved in dry DMSO (10 mL) at 80° C. To this reaction mixture was added isophoron diisocyanate (11.34 g, 51 mmol) while stirring, followed by the addition of two drops of tin octoate. This reaction mixture was stirred overnight at 80° C. The next day, the viscosity of the reaction mixture was lowered by the addition of additional DMSO in order to precipitate the mixture in water. The polymer was collected as a white elastic solid, redissolved in chloroform/methanol (7/3 v/v) and reprecipitated in an excess methanol. The precipitated polymer was dried in vacuo and obtained as a clear tough solid. SEC (DMF, PEG-standards): 14 kDa, D=1.9.

Comparative Example 4: Preparation of Polymer C4

Comparative Example 4 is similar to Example 4, wherein instead of hexamethylene diisocyanate (HDI), methylene dicyclohexane 4,4'-diisocyanate (HMDI) was used.

Telechelic hydroxy terminated polycaprolacton with a molecular weight of 808 Da (10.0 g, 12.4 mmol), 1,6-hexanediol (2.92 g, 24.8 mmol) and UPy-monomer A (2.09 g, 12.4 mmol) were dissolved in dry DMSO (10 mL) at 80° C. To this reaction mixture was added methylene dicyclohexane 4,4'-diisocyanate (HMDI) (13.38 g, 51 mmol) while stirring, followed by the addition of two drops of tin octoate. This reaction mixture was stirred overnight at 80° C. The next day, the viscosity of the reaction mixture was lowered by the addition of additional DMSO in order to precipitate the mixture in water. The polymer was collected as white elastic solid, redissolved in chloroform/methanol (7/3 v/v) and reprecipitated in an excess methanol. The precipitated polymer was dried in vacuo and obtained as a clear tough solid. SEC (DMF, PEG-standards): 13 kDa, D=1.9.

Example 9: Thermal and Mechanical Properties

The following tables show the superior thermal and mechanical properties of the polymers according to this invention when compared to the state of the art.

TABLE 1

Thermal transitions of the Polymers of the Examples above 40° C.

| Polymer No | $T_g$ (° C.) | $T_{m1}$ (° C.) | $T_{m2}$ (° C.) |
| --- | --- | --- | --- |
| 1 | — | 50 | 93 |
| 2 | — | 53 | 116 |
| 3 | — | 59 | 126 |
| 4 | 52 | 111 | — |
| C1 | — | 47 | — |
| C2 | — | 43 | 60 |
| C3 | — | — | — |
| C4 | 62 | — | — |

Thermal data were obtained using Differential Scanning Calorimetry (DSC) with a heating rate of 20° C./min and a heating range from −80° C. to 160° C. Data are based on the first heating runs.

TABLE 2

Mechanical data of the Polymers of the Examples

| Polymer No | $E_{mod}$ (MPa) | $E_{10\%}$ (MPa) | $E_{30\%}$ (MPa) | $E_{100\%}$ (MPa) | Tensile strength (MPa) | Elongation at break |
| --- | --- | --- | --- | --- | --- | --- |
| 1 | 37 | 2.3 | 3.8 | 4.7 | 8.0 | 470% |
| 2 | 30 | 2.1 | 3.6 | 5.7 | 16 | 500% |
| 3 | 80 | 3.6 | 5.0 | 7.0 | 11 | 250% |
| 4 | 77 | 6.5 | 9.3 | 12 | 21 | 320% |
| C1 | 253 | 11.2 | 11.2 | 8.2 | 10 | 470% |
| C2 | 49 | 2.4 | 2.4 | fails | 3.8 | 27% |
| C3 | 360 | 16.6 | 16.3 | 21.4 | 44.9 | 210% |
| C4 | 420 | 22.0 | 20.9 | 27.8 | 45.2 | 265% |

Tensile testing was performed on dog bones cut from solvent casted films according to ASTM D1708-96 specifications in air at room temperature with an elongation rate of 20 mm/min with a preload of 0.02 N.

TABLE 3

Dynamic viscosity of the Polymers of the Examples in solution

| Polymer No | Viscosity (Pa · s) |
|---|---|
| 3 | 0.84 |
| 4 | 4.04 |
| C1 | 0.16 |
| C2 | 0.05 |
| C3 | 6.8 |
| C4 | 34.7 |

Viscosity testing was performed on the polymers dissolved in chloroform/methanol mixtures (10/1 v/v) at 9% weight per volume at 25° C., with a Haake Viscotester 550 equipped with a FL1000 immersion spindle.

Examples of Processing of the Bioresorbable Supramolecular Material

Example 10—Melt Spinning

Polymer 2 of Example 4 was melt spun using by collecting the molten extruded polymer on a rotating drum. This resulted in the formation of long fibres which can be further processed into mats or other woven structures applicable as scaffold for tissue engineering. Extrusion was performed at 140° C. and 90 rpm with a Haake Minilab extruder equipped co-rotating screws and a 0.2 mm die.

Example 11—Electro Spinning

Polymer 3 of Example 5 was dissolved in chloroform/ethanol (95/5) with a concentration of 10 wt %. The resulting solution had a viscosity high enough to allow stable electro-spinning of the solution with the desired fibre thicknesses. The resulting non-wovens can be further used as scaffold materials for tissue engineering. Electro-spinning was performed at 18 kV, 0.05 mL/min, and 15 cm distance.

The invention claimed is:

1. A process for preparing a supramolecular biodegradable polymer for medical implants or scaffolds for cardiovascular applications wherein:

a compound F' that is independently selected from the group consisting of Formulas (7), (8), (9) and (10), or a mixture thereof:

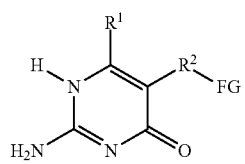
(7)

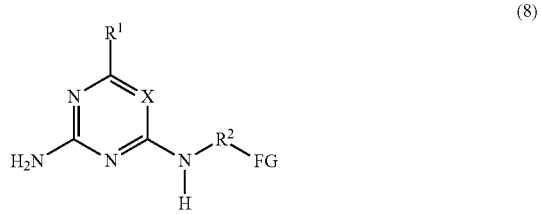
(8)

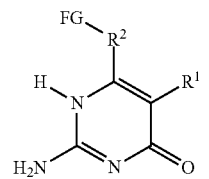
(9)

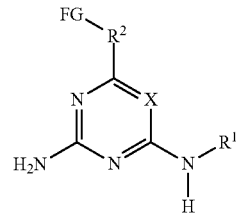
(10)

is reacted with:
a diisocyanate compound C' according to the Formula OCN—R$^6$—NCO;
a polymer A' according to the Formula HO—P—OH that is selected from hydroxy terminated polyethylene glycols, hydroxy terminated polypropylene glycols, hydroxy terminated poly(ethylene-co-propylene) glycols, hydroxy terminated poly(ethylene-block-propylene-block-ethylene) glycols, and hydroxy terminated poly(ethylene-co-tetramethylene) glycols; and
a compound B' according to the Formula HO—R$^5$—OH having a molecular weight of about 56 to about 210 g/mol;
in the presence of a non-reactive non-protic polar organic solvent selected from the group consisting of dioxane, N-methylpyrollidone, dimethyl formamide, dimethylacetamide, dimethyl sulfoxide, propylene carbonate, ethylene carbonate and 2-methoxyethyl-acetate,
wherein the compounds F', C', B', polymer A' and the non-reactive non-protic polar organic solvent together form a reaction mixture, and wherein the amount of the non-reactive non-protic polar organic solvent is at least 20 weight %, based on the total weight of the reaction mixture,
wherein:
X is N or CR$^1$;
R$^1$ is selected from the group consisting of:
(a) hydrogen;
(b) C$_1$-C$_{20}$ alkyl;
R$^2$ is selected from the group consisting of C$_1$-C$_{20}$alkylene;
FG is a functional group independently selected from OH and N(R$^1$)H;
P is a polymeric group having a M$_n$ of about 400 to about 20,000;
R$^5$ is selected from the group consisting of linear C$_2$-C$_{12}$ alkylene groups, wherein the alkylene groups are optionally interrupted by 1-5 heteroatoms selected from the group consisting of O, N and S; and
R$^6$ is selected from the group consisting of linear C$_2$-C$_{16}$ alkylene groups.

2. The process according to claim 1, wherein the supramolecular biodegradable polymer has a number average molecular weight M$_n$ of about 1,200 to about 1,000,000.

3. The process according to claim 1, wherein A', B', C' and F' are reacted in a molar ratio of 1:1:3:1 to 1:6:8:1, in which the molar amount of C' is always equal to 0.8 to 1.2 times the total molar amount of A' plus B' plus F'.

4. The process according to claim 1, wherein FG is OH.

5. The process according to claim 1, wherein compound C' according to Formula OCN—$R^6$—NCO is 1,6-hexane diisocyanate.

6. The process according to claim 1, wherein polymer A' is a hydroxy terminated polyethylene glycol, polypropylene glycol, or poly(ethylene-block-propylene-block-ethylene) glycol.

7. The process according to claim 1, wherein compound B' according to formula HO—$R^5$—OH is 1,6-hexane diol.

8. The process according to claim 1, wherein compound F' is according to Formula (7).

9. The process according to claim 1, wherein P is a polymeric group having a $M_n$ of about 600 to about 2,500.

10. A supramolecular biodegradable polymer for medical implants or scaffolds for cardiovascular applications, said supramolecular biodegradable polymer having a modulus at 30% elongation that is at least 1.2 times the modulus at 10% elongation according to test method ASTM D 1708-96 at room temperature with a crosshead speed of 20 mm/min, the supramolecular biodegradable polymer comprising structural units A, B, C and F, wherein:

structural units A are represented by divalent organic groups —P—, wherein P is a polymeric group having a $M_n$ of about 400 to about 20,000 and wherein structural units A are selected from polyethylene glycol, polypropylene glycol, poly(ethylene-co-propylene glycol), poly(ethylene-block-propylene-block-ethylene) glycol, and poly(ethylene-co-tetramethylene) glycol units;

structural units B are represented by divalent organic groups —$R^5$—, wherein $R^5$ is selected from the group consisting of $C_2$-$C_{12}$ alkylene, which are optionally interrupted by 1-5 heteroatoms selected from the group consisting of O, N and S;

structural units C are represented by divalent organic groups —$R^6$—, wherein $R^6$ is —$(CH_2)_6$—;

structural units F are independently selected from the group consisting of units according to Formulas (1), (2), (3) and (4):

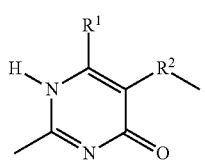 (1)

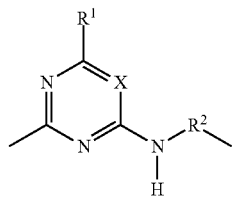 (2)

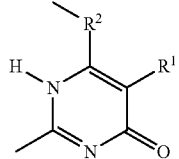 (3)

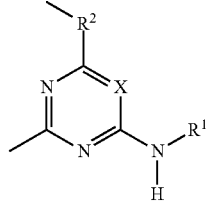 (4)

X is N or $CR^1$;
$R^1$ is selected from the group consisting of:
 (a) hydrogen;
 (b) $C_1$-$C_{20}$ alkyl;
$R^2$ is selected from the group consisting of $C_1$-$C_{20}$ alkylene; and
wherein structural units C and F are bonded to each other via groups independently selected from urethane and urea groups, wherein structural units A and B are bonded to other structural units via urethane groups only and wherein F is bonded via the 2-position of the pyrimidine moiety or via the 2-position of the triazine moiety by a urea moiety.

11. The supramolecular biodegradable polymer according to claim 10, wherein structural units A are polyethylene glycol, polypropylene glycol, or poly(ethylene-block-propylene-block-ethylene) glycol units.

12. The supramolecular biodegradable polymer according to claim 10, wherein $R^5$ is —$(CH_2)_6$—.

13. The supramolecular biodegradable polymer according to claim 10, wherein structural unit F is according to Formula (1).

14. The supramolecular biodegradable polymer according to claim 10, wherein P is a polymeric group having a $M_n$ of about 600 to about 2,500.

15. A medical implant or scaffold for cardiovascular applications comprising a supramolecular biodegradable polymer according to claim 10.

16. The scaffold according to claim 15, wherein the scaffold is a heart valve or a vascular graft.

* * * * *